US010786605B2

(12) United States Patent
Fruci et al.

(10) Patent No.: US 10,786,605 B2
(45) Date of Patent: Sep. 29, 2020

(54) INFECTION FIGHTING DRUG ELUTING LEAD BOOT

(71) Applicant: Cardiac Pacemakers, Inc., St. Paul, MN (US)

(72) Inventors: Angelo Fruci, Mahtomedi, MN (US); Arthur J. Foster, Blaine, MN (US); Joseph T. Delaney, Jr., Minneapolis, MN (US); Danielle Frankson, Dayton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 225 days.

(21) Appl. No.: 15/840,815

(22) Filed: Dec. 13, 2017

(65) Prior Publication Data

US 2018/0169306 A1   Jun. 21, 2018

Related U.S. Application Data

(60) Provisional application No. 62/435,826, filed on Dec. 18, 2016.

(51) Int. Cl.
*A61L 31/16* (2006.01)
*A61N 1/05* (2006.01)
(Continued)

(52) U.S. Cl.
CPC .............. *A61L 31/16* (2013.01); *A61L 31/06* (2013.01); *A61N 1/05* (2013.01); *A61N 1/0587* (2013.01);
(Continued)

(58) Field of Classification Search
CPC ...... A61L 31/16; A61N 1/0587; A61N 1/3752
(Continued)

(56) References Cited

U.S. PATENT DOCUMENTS 4,676,782 A   6/1987   Yamamoto et al.
5,154,182 A   10/1992  Moaddeb
(Continued)

FOREIGN PATENT DOCUMENTS

WO   WO9307924 A1    4/1993
WO   WO2008134478 A2   11/2008

OTHER PUBLICATIONS

H1465. Implantable Lead Infection Barrier. Jul. 4, 1995. Stokes, et. al. 4 pages.
(Continued)

*Primary Examiner* — Amanda K Hulbert
*Assistant Examiner* — Philip C Edwards
(74) *Attorney, Agent, or Firm* — Faegre Drinker Biddle & Reath LLP

(57) ABSTRACT

An implantable medical electrical lead is connectable to an electrical header of an implantable pulse generator. The lead includes a lead body, at least one electrode, a lead terminal, and a lead boot. The lead body extends from a proximal end to a distal end. The at least one electrode is disposed at the distal end of the lead body. The lead terminal is disposed at the proximal end of the lead body and configured to connect the lead to the electrical header. The lead boot is formed of an elastic polymer infused with at least one antibiotic drug. A portion of the lead boot is configured to be disposed within the electrical header when the lead is connected to the electrical header.

4 Claims, 3 Drawing Sheets

(51) Int. Cl.
*A61N 1/36* (2006.01)
*A61L 31/06* (2006.01)
*A61N 1/375* (2006.01)
*A61N 1/08* (2006.01)
*A61N 1/372* (2006.01)
*B29C 69/00* (2006.01)
*B29K 75/00* (2006.01)
*B29K 83/00* (2006.01)
*B29K 101/12* (2006.01)
*B29L 31/00* (2006.01)

(52) U.S. Cl.
CPC ............ *A61N 1/36* (2013.01); *A61N 1/3752* (2013.01); *A61L 2300/406* (2013.01); *A61N 1/08* (2013.01); *A61N 1/372* (2013.01); *B29C 69/00* (2013.01); *B29K 2075/00* (2013.01); *B29K 2083/00* (2013.01); *B29K 2101/12* (2013.01); *B29K 2995/0056* (2013.01); *B29L 2031/753* (2013.01)

(58) Field of Classification Search
USPC .......................................................... 607/115
See application file for complete search history.

(56) References Cited

U.S. PATENT DOCUMENTS

| | | | |
|---|---|---|---|
| 5,217,493 A | 6/1993 | Raad et al. | |
| 5,861,023 A | 1/1999 | Vachon | |
| 6,267,782 B1 | 7/2001 | Ogle et al. | |
| 6,451,003 B1 | 9/2002 | Prosl et al. | |
| 7,067,606 B2 | 6/2006 | Mather et al. | |
| 7,174,221 B1 | 2/2007 | Chen et al. | |
| 7,322,965 B2 | 1/2008 | Gibson et al. | |
| 7,507,230 B2 | 3/2009 | Li et al. | |
| 7,682,202 B2 | 3/2010 | Arnholt et al. | |
| 7,947,301 B2 | 5/2011 | Bischoff et al. | |
| 8,209,016 B2 | 6/2012 | Deininger et al. | |
| 8,308,713 B2 | 11/2012 | Li et al. | |
| 8,430,852 B2 | 4/2013 | Bischoff et al. | |
| 8,628,798 B2 | 1/2014 | Halliday et al. | |
| 2004/0186628 A1 | 9/2004 | Ries et al. | |
| 2005/0181977 A1 | 8/2005 | Hunter et al. | |
| 2007/0099518 A1* | 5/2007 | Arnholt ................ | A61N 1/3752 439/675 |
| 2009/0198197 A1* | 8/2009 | Bischoff ................ | A61K 31/65 604/265 |
| 2010/0241205 A1* | 9/2010 | Deininger ................ | A61N 1/05 607/116 |
| 2015/0290280 A1* | 10/2015 | Petrak ..................... | A61L 15/46 604/151 |

OTHER PUBLICATIONS

International Search Report and Written Opinion issued in PCT/US2017/066149, dated Mar. 6, 2018, 11 pages.

* cited by examiner

INFECTION FIGHTING DRUG ELUTING LEAD BOOT

CROSS-REFERENCE TO RELATED APPLICATION

This application claims priority to Provisional Application No. 62/435,826, filed Dec. 18, 2016, which is herein incorporated by reference in its entirety.

TECHNICAL FIELD

The present invention relates to preventing infections associated with implantable medical devices. More specifically, the invention relates to an infection fighting drug eluting lead boot for an implantable medical electrical lead.

BACKGROUND

Medical devices may be implanted in a subcutaneous pocket to support sensing intrinsic physiological electrical activity, delivering a therapeutic stimulus to patient tissue, or providing other therapy to specific treatment sites. For example, a pulse generator may be implanted in a subcutaneous pocket in a patient's chest, with one or more electrical leads extending from the pulse generator to treatment sites within the patient.

Implanting a medical device within a patient exposes the patient to a risk of a nosocomial (e.g., hospital-acquired) infection associated with bacteria adhering to the exterior of the medical device when it is placed within the subcutaneous pocket, causing a pocket infection. For example, the average nosocomial infection rate associated with the implantation of cardiovascular implantable electronic devices in 2008 was approximately 2.4 percent. In some cases of infection, the implantable medical device, including the device housing and any associated electrical leads, must be completely removed. Following removal, the infection must be cured and the patient must heal enough to tolerate implantation of a replacement medical device. The costs of such infections may be significant, not only intrinsically, but also in terms of the physical and emotional stress suffered by the patient.

What is needed is a way to reduce the occurrence of infections which may result from implanting a medical device within a patient.

SUMMARY

Example 1 is an implantable medical electrical lead connectable to an electrical header of an implantable pulse generator. The lead includes a lead body, at least one electrode, a lead terminal, and a lead boot. The lead body extends from a proximal end to a distal end. The at least one electrode is disposed at the distal end of the lead body. The lead terminal is disposed at the proximal end of the lead body and configured to connect the lead to the electrical header. The lead boot is formed of an elastic polymer infused with at least one antibiotic drug. A portion of the lead boot is configured to be disposed within the electrical header when the lead is connected to the electrical header.

Example 2 is the lead of Example 1, wherein the lead boot extends over a portion of the proximal end of the lead body and a portion of the lead terminal.

Example 3 is the lead of either of Examples 1 or 2, wherein the at least one antibiotic drug includes at least one of minocycline and rifampin.

Example 4 is the lead of any of Examples 1-3, wherein the elastic polymer of the lead boot is selected from the group consisting of a silicone polymer and a polyurethane polymer.

Example 5 is the lead of any of Examples 1-4, wherein the lead terminal includes a lead terminal body and at least one electrical contact electrically connected to the at least one electrode.

Example 6 is the lead of Example 5, wherein the lead terminal body is formed of an electrically non-conductive polymer.

Example 7 is the lead of any of Examples 1-6, wherein the lead boot is secured to the lead body and the lead terminal by an adhesive.

Example 8 is the lead of any of Examples 1-6, wherein the lead boot is molded onto the lead body and the terminal.

Example 9 is an Implantable medical device including a pulse generator and an electrical lead according to any of Examples 1-8. The pulse generator includes a housing and an electrical header connected to the housing. The electrical header includes a lead port. The lead terminal is inserted into the lead port to connect the lead to the electrical header. A portion of the lead boot is disposed within the lead port.

Example 10 is the device of Example 9, wherein the lead port includes at least one port contact electrically connecting the lead terminal to the pulse generator.

Example 11 is a method of forming an electrical lead connectable to an electrical header of an implantable pulse generator, the electrical lead including a lead body, a lead terminal connected to the lead body, and a drug eluting lead boot formed of an elastic polymer. The method includes disposing the lead boot over a portion of the lead body and a portion of the lead terminal so that a portion of the lead boot is disposed within the electrical header when the lead is connected to the electrical header, and infusing the lead boot with at least one antibiotic drug.

Example 12 is the method of Example 11, wherein disposing the lead boot over the portion of the lead body and the portion of the lead terminal includes adhering the lead boot to the portion of the lead body and the portion of the lead terminal by molding the lead boot, applying an adhesive to the portion of the lead body and the portion of the lead terminal, and positioning the molded lead boot over the portion of the lead body and the portion of the lead terminal.

Example 13 is the method of Example 11, wherein disposing the lead boot over the portion of the lead body and the portion of the lead terminal includes molding the lead boot over the portion of the lead body and the portion of the lead terminal.

Example 14 is the method of any of Examples 11-13, wherein infusing the lead boot with at least one antibiotic drug includes treating the lead boot with at least one of hexane or heptane to swell the lead boot, and immersing the swollen lead boot in a solution containing the at least one antibiotic drug to infuse the at least one antibiotic drug into the lead boot.

Example 15 is the method of any of Examples 11-13, wherein infusing the lead boot with at least one antibiotic drug includes mixing the at least one antibiotic into the elastic polymer before molding the lead boot.

Example 16 is an implantable medical electrical lead connectable to an electrical header of an implantable pulse generator. The lead includes a lead body, at least one electrode, a lead terminal and a lead boot. The lead body extends from a proximal end to a distal end. The at least one electrode is disposed at the distal end of the lead body. The lead terminal is disposed at the proximal end of the lead body and configured to connect the lead to the electrical header. The lead boot extends over a portion of the proximal end of the lead body and a portion of the lead terminal. A portion of the lead boot is configured to be disposed within the electrical header when the lead is connected to the electrical header. The lead boot is formed of an elastic polymer infused with at least one antibiotic drug.

Example 17 is the lead of Example 16, wherein the at least one antibiotic drug includes at least one of minocycline and rifampin.

Example 18 is the lead of either of Examples 16 and 17, wherein the elastic polymer of the lead boot is selected from the group consisting of a silicone polymer and a polyurethane polymer.

Example 19 is the lead of any of Examples 16-18, wherein the lead terminal includes a lead terminal body, and at least one electrical contact electrically connected to the at least one electrode.

Example 20 is the lead of Example 19, wherein the lead terminal body is formed of an electrically non-conductive polymer.

Example 21 is the lead of any of Examples 16-20, wherein the lead boot is secured to the lead body and the lead terminal by an adhesive.

Example 22 is the lead of any of Examples 16-21, wherein the lead boot is molded onto the lead body and the terminal.

Example 23 is an implantable medical device including a pulse generator and an electrical lead. The pulse generator includes a housing and an electrical header connected to the housing. The electrical header includes a lead port. The electrical lead is physically and electrically connected to the electrical header. The electrical lead includes a lead body, at least one electrode, a lead terminal, and a lead boot. The lead body extends from a proximal end to a distal end. The at least one electrode is disposed at the distal end of the lead body. The lead terminal is disposed at the proximal end of the lead body. The lead terminal is inserted into the lead port to connect the lead to the electrical header. The lead boot extends over a portion of the proximal end of the lead body and a portion of the lead terminal. A portion of the lead boot is disposed within the lead port. The lead boot is formed of an elastic polymer infused with at least one antibiotic drug.

Example 24 is the device of Example 23, wherein the at least one antibiotic drug includes at least one of minocycline and rifampin.

Example 25 is the device of either of Examples 23 and 24, wherein the elastic polymer of the lead boot is selected from the group consisting of a silicone polymer and a polyurethane polymer.

Example 26 is the device of any of Examples 23-25, wherein the lead terminal includes a lead terminal body, and at least one terminal contact electrically connected to the at least one electrode.

Example 27 is the device of Example 26, wherein the lead port includes at least one port contact electrically connecting the at least one terminal contact to the pulse generator.

Example 28 is the device of either of Examples 26 or 27, wherein the lead terminal body is formed of an electrically non-conductive polymer.

Example 29 is the device of any of Examples 23-28, wherein the lead boot is secured to the lead body and the lead terminal by an adhesive.

Example 30 is the device of any of Examples 23-29, wherein the lead boot is molded onto the lead body and the terminal.

Example 31 is a method of forming an electrical lead connectable to an electrical header of an implantable pulse generator, the electrical lead including a lead body, a lead terminal connected to the lead body, and a drug eluting lead boot formed of an elastic polymer. The method including disposing the lead boot over a portion of the lead body and a portion of the lead terminal so that when the lead is connected to the electrical header a portion of the lead boot is disposed within the electrical header, and infusing the lead boot with at least one antibiotic drug.

Example 32 is the method of Example 31, wherein disposing the lead boot over the portion of the lead body and the portion of the lead terminal includes adhering the lead boot to the portion of the lead body and the portion of the lead terminal by molding the lead boot, applying an adhesive to the portion of the lead body and the portion of the lead terminal, and positioning the molded lead boot over the portion of the lead body and the portion of the lead terminal.

Example 33 is the method of Example 31, wherein disposing the lead boot over the portion of the lead body and the portion of the lead terminal includes molding the lead boot over the portion of the lead body and the portion of the lead terminal. Example 34 is the method of any of Examples 31-33, wherein infusing the lead boot with at least one antibiotic drug includes treating the lead boot with at least one of hexane or heptane to swell the lead boot, and immersing the swollen lead boot in a solution containing the at least one antibiotic drug to infuse the at least one antibiotic drug into the lead boot.

Example 35 is the method of any of Examples 31-33, wherein infusing the lead boot with at least one antibiotic drug includes mixing the at least one antibiotic into the elastic polymer before molding the lead boot.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
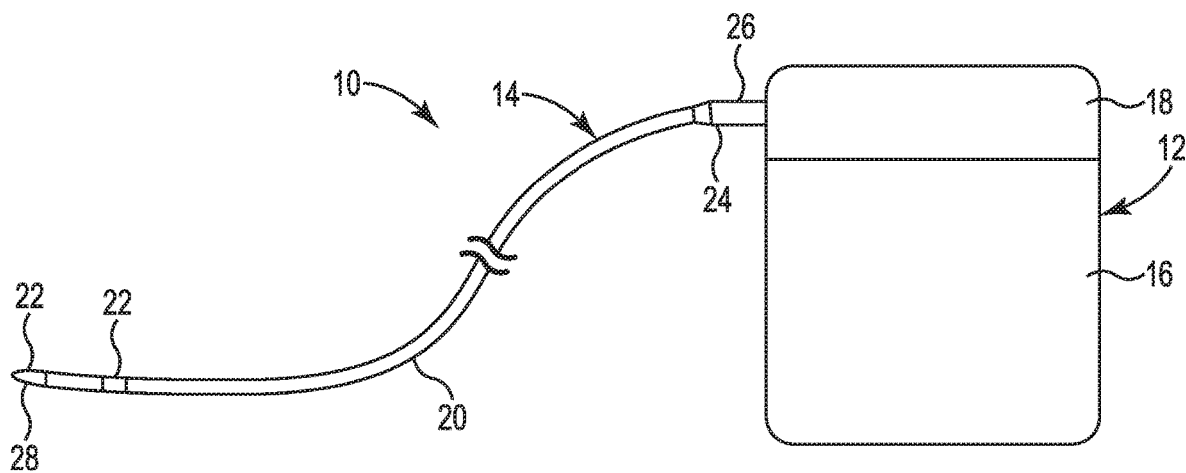
FIG. 1 is a side view of an implantable medical device in accordance with some embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention.

The detailed description of the invention which follows is intended to illustrate but not limit the invention.

In accordance with various aspects of the disclosure, a medical device is defined as "an implantable medical device" if it is completely or partly introduced, surgically or medically, into the human body or by medical intervention into a natural orifice, and which is intended to remain after the procedure. It is understood that the various embodiments can be implemented in any suitable medical device implanted in a patient that include a housing and an electrical lead electrically connected to the housing, such as the cardiac rhythm management (CRM) system described below. For example, embodiments may be employed with a subcutaneously-implanted implantable cardioverter-defibrillator (ICD) housing and lead system. Other such implantable medical devices include, without limitation, implantable cardiac monitors and neurostimulation systems such as spinal cord stimulation or deep brain stimulation devices.

FIG. 1 is a side view of an implantable medical device in accordance with some embodiments of the disclosure. FIG. 1 shows a cardiac rhythm management (CRM) system 10 for delivering and/or receiving electrical pulses or signals to stimulate, shock, and/or sense a heart (not shown). The CRM system 10 can include a pulse generator 12 and a lead 14. The pulse generator 12 includes a housing 16 and an electrical header 18 connected to the housing 16. The housing 16 can include a source of power as well as electronic circuitry. The electrical header 18 provides a physical and electrical connection for the lead 14, as detailed below in reference to FIGS. 3 and 4. The connection provided by the electrical header 18 permits the lead 14 to be selectively connected and disconnected to the pulse generator 12. The pulse generator 12 may be a battery-powered device that generates a series of timed electrical discharges or pulses. The pulse generator 12 may be implanted into a subcutaneous pocket made in the wall of the chest. Alternatively, the pulse generator 12 may be placed in a subcutaneous pocket made in the abdomen, or in another location. It should be noted that while the lead 14 is described for use with the heart, the lead 14 is suitable for other forms of electrical stimulation/sensing as well.

The lead 14 can include a lead body 20, at least one electrode 22 (two shown in FIG. 1), and a lead boot 24. The lead body 20 can be flexible, tubular structure formed of a biocompatible polymer, such as silicone or polyurethane, such as polyisobutylene-polyurethane. The electrode 22 can be formed of a biocompatible conductor, such as titanium, stainless steel, iridium, iridium oxide, titanium nitride, platinum, a conductive polymer or combinations of any of these materials, to name a few. The lead boot 24 is described in detail below in reference to FIG. 2.

The lead body 20 extends generally from a proximal end 26 to a distal end 28. The at least one electrode 22 can be disposed along a portion of the lead 14, for example near the distal end 28, to electrically couple the lead 14 with the heart. At least one electrical conductor (not shown) may be disposed within the lead body 20 and extend generally from the proximal end 26 to the distal end 28. The at least one electrical conductor electrically connects the electrode 22 with the proximal end 26 of the lead 14 to couple the electrode 22 to the pulse generator 12. So configured, the lead 14 may carry electrical current and pulses between the pulse generator 12 and the heart.

Figure 2:
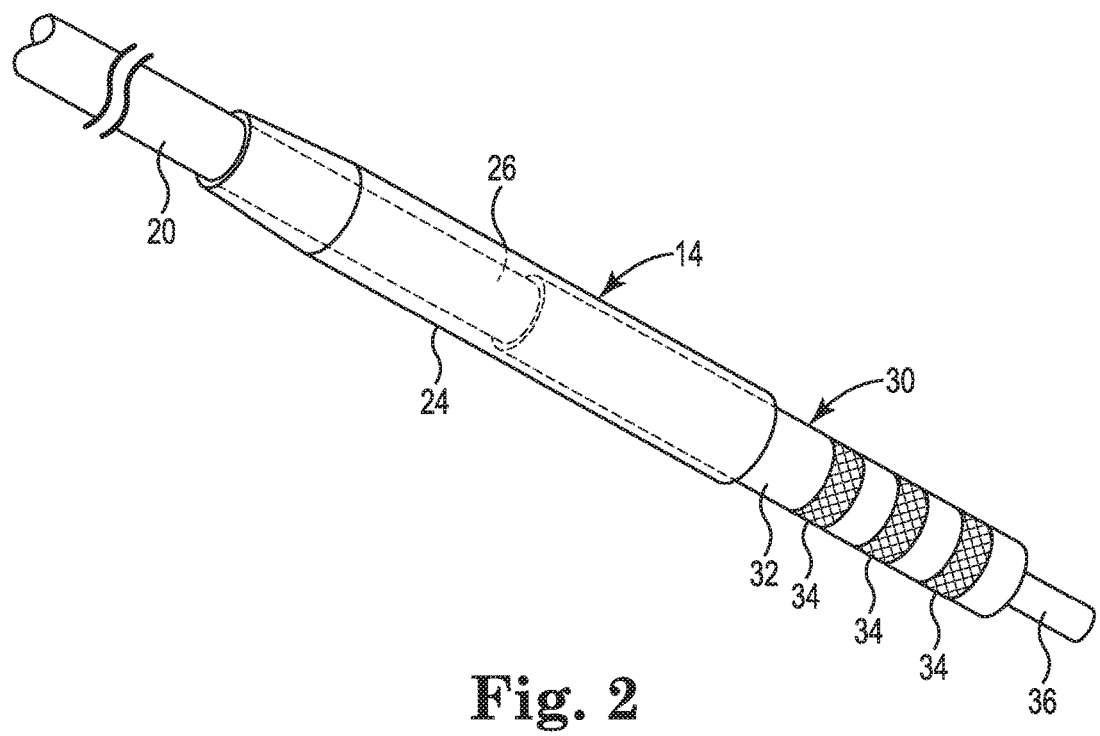
FIG. 2 is a partial perspective view of a portion of a medical electrical lead in accordance with some embodiments of the disclosure.

FIG. 2 is a partial perspective view of a portion of the lead 14, in accordance with some embodiments of the disclosure. FIG. 2 shows a portion of the lead 14 at the proximal end 26 with the lead 14 disconnected from the pulse generator 12. As shown in FIG. 2, the lead 14 further includes a lead terminal 30 disposed at the proximal end 26 of the lead body 20. The lead terminal 30 can include a lead terminal body 32, at least one electrical contact 34 (three shown), and a terminal pin 36, which may also act as an electrical contact. The lead terminal body 32 can be a tubular structure formed of a biocompatible non-conductive polymer such as, for example, an aromatic polyether-based thermoplastic polyurethane, polyether ether ketone, a polycarbonate based polyurethane, silicone rubbers, or a hybrid material composed of silicones and polyurethanes. The at least one electrical contact 34 and the terminal pin 36 may be formed of a conductive metal, for example, stainless steel, titanium and its alloys, platinum and its alloys, palladium and its alloys, tantalum and its alloys, and nickel cobalt alloys, such as MP35N. In the embodiment shown in FIG. 2, the at least one electrical contact 34 extends circumferentially around at least a portion of the lead terminal body 32. The terminal pin 36 is disposed at an end of the lead terminal body 32 opposite the lead body 20. Other embodiments may have greater or fewer electrical contacts 34 and/or may not have a terminal pin 36. The at least one electrical conductor (not shown) disposed within the lead body 20 may extend through the lead terminal body 32 to the at least one electrical contact 34 and/or to the terminal pin 36 to electrically connect the at least one electrode 22 with the at least one electrical contact 34 and/or terminal pin 36 in lead terminal 30.

The lead boot 24 can physically contact and extend over a portion of the proximal end 26 of the lead body 20 and over a portion of the lead terminal 30, as shown in FIG. 2. So disposed, the lead boot 24 provides mechanical strain relief of the transition from the lead terminal 30 to the flexible lead body 20 when the lead 14 is connected to the pulse generator 12.

The lead boot 24 can be formed of an elastic polymer, that is, a polymer having a glass-transition temperature below room temperature, such as a silicone polymer, a polyurethane polymer, or a hybrid material composed of silicone and polyurethane. The elastic polymer of the lead boot 24 is infused with at least one antibiotic drug such that the at least one antibiotic drug can elute from the elastic polymer of the lead boot 24. The eluting antibiotic drug can weaken or kill bacteria adhering to the surface of the boot as a result of the boot being set down on operating spaces and/or being moved around during implantation of the CRM system 10. Once the CRM system 10 is implanted, the at least one antibiotic drug can continue to elute within the subcutaneous pocket to reduce incidence and/or severity of a pocket infection.

In some embodiments, the at least one antibiotic drug can include a broad-spectrum antibiotic drug, such as minocycline; or a narrow-spectrum antibiotic drug, such as rifampin. In some embodiments, the at least one antibiotic drug can include a combination of a broad-spectrum antibiotic drug and a narrow-spectrum antibiotic drug, such as a combination of minocycline and rifampin. In other embodiments, the at least one antibiotic drug can include tetracyclines, penicillins, macrolides, rifampin and combinations of thereof.

Figure 3:
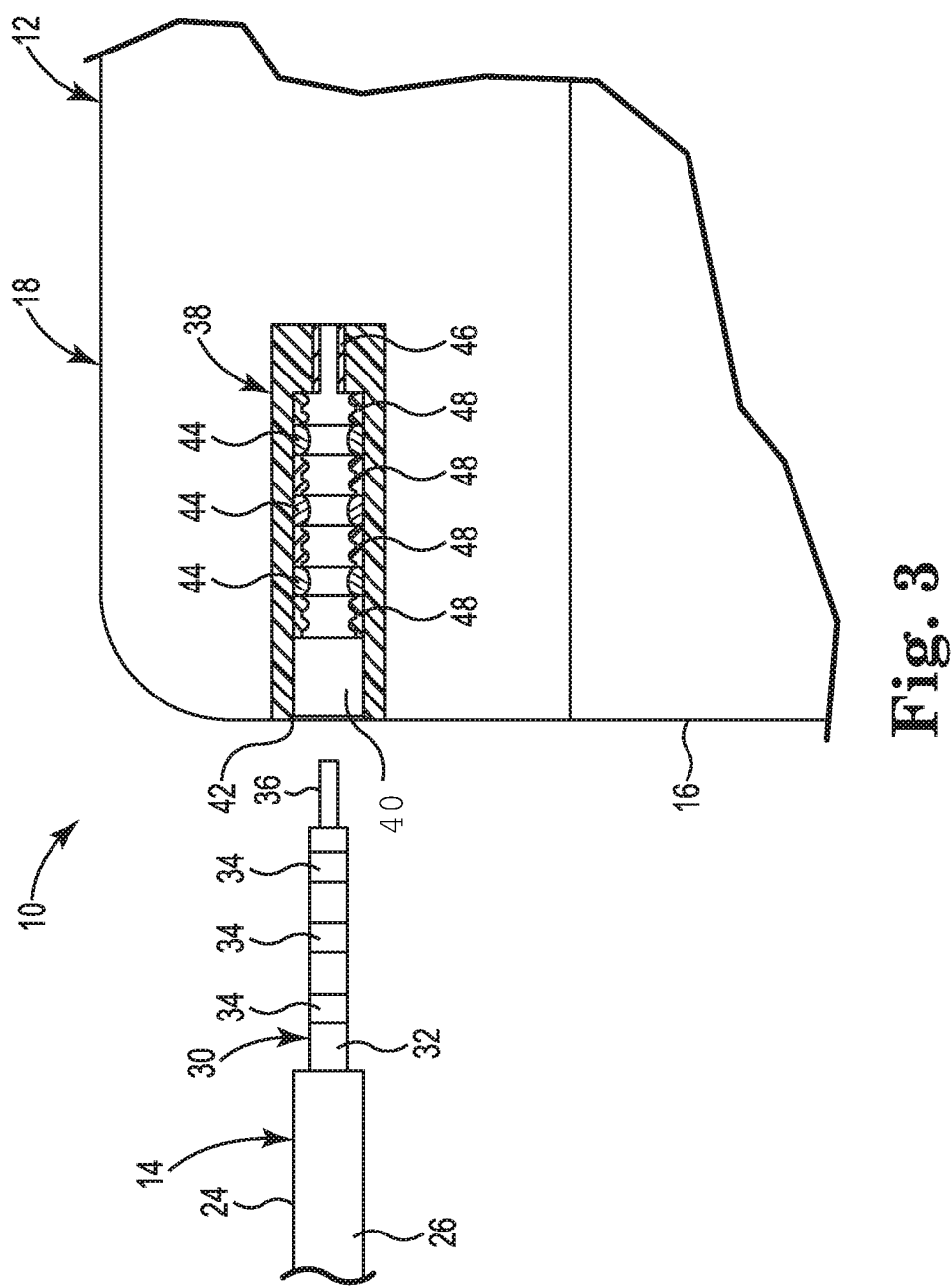
FIG. 3 is a schematic cross-sectional view of a portion of an implantable medical device in accordance with some embodiments of the disclosure.

FIG. 3 is a schematic cross-sectional view of a portion of an implantable medical device, the CRM system 10, in accordance with some embodiments of the disclosure. FIG. 3 shows the lead 14 disconnected from the electrical header 18 of the pulse generator 12. As shown in FIG. 3, the electrical header 18 includes a lead port 38. The lead port 38 can be formed of a rigid polymer, that is, a polymer having a glass-transition temperature greater than body temperature, about 37° C. The rigid polymer is a non-conductive polymer such as, for example, an aromatic polyether-based thermoplastic polyurethane, polyether ether ketone, or a polyethersulfone. The lead port 38 can form a lumen 40 extending at least partially through the lead port 38 with an opening 42 in the lumen 40 at an exterior surface of the electrical header 18. The lead port 38 can include at least one port contact 44 (three shown in FIG. 3) and, optionally, a terminal pin contact 46 contained within the lumen 40. The at least one port contact 44 and the terminal pin contact 46 can be spring contacts extending at least partially circumferentially around the lumen 40 and is in contact with the surface thereof. In some embodiments, the at least one port contact 44 and the terminal pin contact 46 can be formed of a biocompatible, resilient conductor, such as a nickel-cobalt based alloy, titanium or titanium alloys, or stainless steel. The at least one port contact 44 and, optionally, the terminal pin contact 46, can be electrically connected to the source of power and the electronic circuitry contained within the housing 16.

In some embodiments, the lead port 38 may further include at least one seal 48 (four shown in FIG. 3). The at least one seal 48 can be formed of a biocompatible, elastomeric polymer. The at least one seal 48 can extend circumferentially around the lumen 40 and is in contact with the surface thereof. In the embodiment shown in FIG. 3, each of the four seals 48 are disposed adjacent to at least one of the three port contacts 44 and the terminal pin contact 46.

Figure 4:
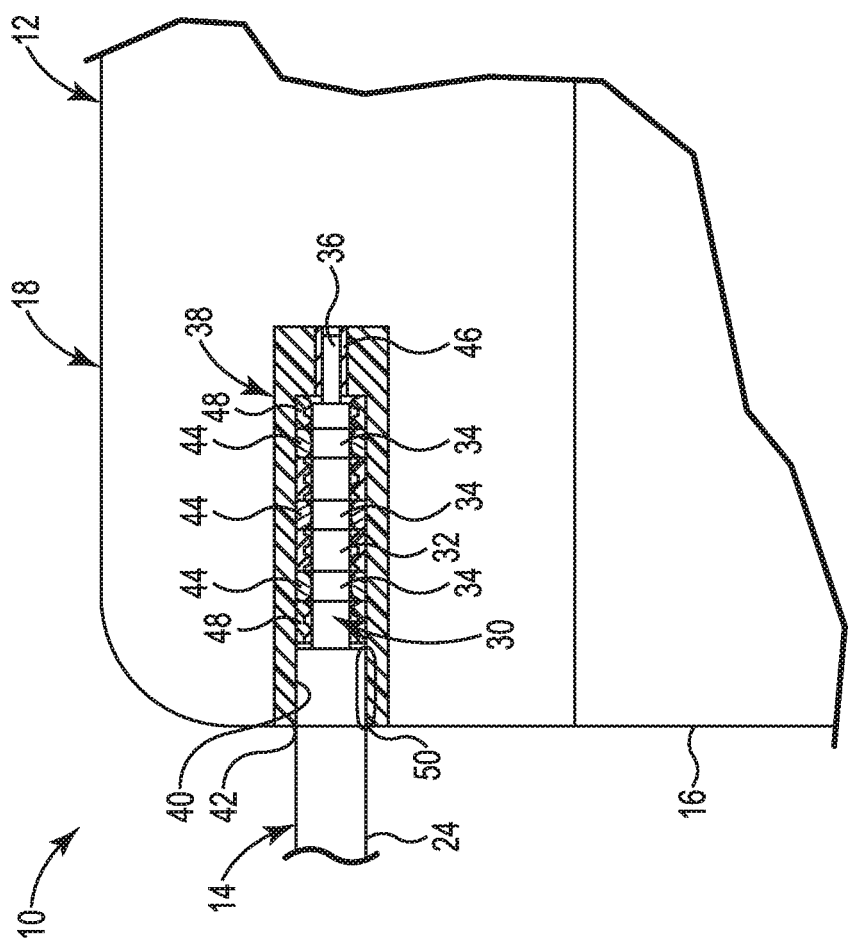
FIG. 4 is another schematic cross-sectional view of the portion of the implantable medical device of FIG. 3, according to some embodiments of the disclosure.

FIG. 4 is another schematic cross-sectional view of the portion of the CRM system 10 of FIG. 3. FIG. 4 shows the lead 14 connected to the electrical header 18 of the pulse generator 12. As shown in FIG. 4, at least a portion of the lead terminal 30 is inserted into the lumen 40 of the lead port 38 until each of the three electrical contacts 34 is aligned with a different one of the three port contacts 44, and the terminal pin 36 is aligned with the terminal pin contact 46.

The port contacts 44 are sized such that an inner diameter of the contact is smaller than an outer diameter of the electrical contacts 34 to insure spring tension is applied by the port contacts 44 to facilitate a reliable electrical connection between the electrical contacts 34 and the port contacts 44. Similarly, the terminal pin contact 46 is sized such that an inner diameter of the terminal pin contact 46 is smaller than an outer diameter of the terminal pin 36 to facilitate a reliable electrical connection between the terminal pin 36 and the terminal pin contact 46. The seals 48 are sized such that in inner diameter of the seal 48 is smaller than an outer diameter of the lead terminal body 32 to facilitate a fluid-tight seal between the lead terminal body 32 and the seal 48.

Thus, as shown in FIG. 4 and described above, the lead terminal 30 is configured to connect the lead 14 to the electrical header 18 of the pulse generator 12.

As shown in FIG. 4, a portion of the lead boot 24 is configured to be disposed within the electrical header 18 when the lead 14 is connected to the electrical header 18. Specifically, when the lead terminal 30 is inserted into the opening 42 of the lumen 40 of the lead port 38 to connect the lead 14 to the electrical header 18, a portion of the lead boot 24 is disposed within the lumen 40 of the lead port 38. In some embodiments, the physical proximity thus established between the portion of the lead boot 24 disposed within the lead port 38 and the lead port 38 can provide additional mechanical support for the connection between the lead 14 and the electrical header 18.

The physical proximity between the portion of the lead boot 24 disposed within the lead port 38 and the lead port 38 can also form a tight, closed-in crevasse 50 between the lead boot 24 and the lead port 38. The crevasse 50 can provide a protected environment for bacterial growth, shielding much of an infection within the crevasse 50 from an antibiotic treatment applied externally to the pulse generator 12 and the lead 14 either before or after they are implanted within the subcutaneous pocket. However, because the lead boot 24 is infused with the at least one antibiotic drug which elutes from the lead boot 24, an antibiotic treatment is provided from the lead boot 24 along the entire length of the crevasse 50. Further, the drug eluting lead boot 24 disposed within the lead port 38 can also protect the entire lumen 40 from bacterial infection, by eluting the at least one antibiotic into the lumen 40 and by stopping bacteria at the opening 42 from entering the lumen 40. In this way, embodiments of the disclosure may reduce the occurrence of infections which may result from implanting a medical device, such as CRM system 10, within a patient by preventing the proliferation of bacteria that would otherwise form in the crevasse 50 between the lead boot 24 and the electrical header 18.

The lead 14 as described above may be formed by disposing the lead boot 24 over the portion of the lead body 20 and the lead terminal 30, and infusing the lead boot 24 with the at least one antibiotic drug. The lead boot 24 is disposed so that when the lead 14 is connected to the electrical header 18, a portion of the lead boot 24 is disposed within the electrical header 18.

In some embodiments, disposing the lead boot 24 over the portion of the lead body 20 and the portion of the lead terminal 30 includes adhering the lead boot 24 to the portion of the lead body 20 the portion of the lead terminal 30 by forming the lead boot 24, applying an adhesive to the portion of the lead body 20 and the portion of the lead terminal 30, and positioning the formed lead boot 24 over the portion of the lead body 20 and the portion of the lead terminal 30. The lead boot 24 can be formed by, for example, molding, casting or 3D printing. In some embodiments, the adhesive is applied before the lead boot 24 is positioned over the portion of the lead body 20 and the portion of the lead terminal 30. In some other embodiments, the lead boot 24 is positioned over the portion of the lead body 20 and the portion of the lead terminal 30, and then an adhesive is applied to the portion of the lead body 20 and the portion of the lead terminal 30 either through a plurality of holes in the lead boot 24 positioned along the length of the lead boot 24, or with a hypodermic needle inserted between the lead boot 24 and the portion of the lead body 20 and the portion of the lead terminal 30. In other embodiments, disposing the lead boot 24 over the portion of the lead body 20 and the portion of the lead terminal 30 includes directly molding the lead boot 24 over the portion of the lead body 20 and the portion of the lead terminal 30.

In some embodiments, infusing the lead boot 24 with the at least one antibiotic drug can include treating the lead boot 24 with a swelling agent to swell the lead boot 24, and then immersing the swollen lead boot 24 in a solution containing the at least one antibiotic drug to infuse the at least one antibiotic drug into the lead boot 24. in some embodiments. Swelling agents can include at least one of hexane, heptane, and some halocarbons. In some embodiments, swelling can be done at about room temperature. In some embodiments, swelling and immersion times can each range from as short as 2 minutes, 3 minutes, 5 minutes, or 7 minutes, or as long as 10 minutes, 15 minutes, 20 minutes, or 30 minutes, or within any range defined by any two of the preceding values.

In some embodiments, infusing the lead boot 24 with at least one antibiotic drug can include mixing the at least one antibiotic into the elastic polymer used to form the lead boot 24 before molding the lead boot 24.

For the sake of clarity, the embodiments described above and shown in FIGS. 1-4 include the single lead 14 and the electrical header 18 having a single lead port 38. However, it is understood that embodiments may have more than one lead 14 and more than one lead port 38.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of forming an electrical lead connectable to an electrical header of an implantable pulse generator, the electrical lead including a lead body, a lead terminal connected to the lead body, and a drug eluting lead boot formed of an elastic polymer, the method comprising:
    disposing the lead boot over a portion of the lead body and a portion of the lead terminal so that when the lead is connected to the electrical header, a portion of the lead boot is disposed within the electrical header; and
    infusing the lead boot with at least one antibiotic drug, wherein infusing the lead boot with at least one antibiotic drug includes:
        treating the lead boot with at least one of hexane or heptane to swell the lead boot; and
        immersing the swollen lead boot in a solution containing the at least one antibiotic drug to infuse the at least one antibiotic drug into the lead boot.

2. The method of claim 1, wherein disposing the lead boot over the portion of the lead body and the portion of the lead terminal includes adhering the lead boot to the portion of the lead body and the portion of the lead terminal by:
    molding the lead boot;
    applying an adhesive to the portion of the lead body and the portion of the lead terminal; and
    positioning the molded lead boot over the portion of the lead body and the portion of the lead terminal.

3. The method of claim 1, wherein disposing the lead boot over the portion of the lead body and the portion of the lead terminal includes molding the lead boot over the portion of the lead body and the portion of the lead terminal.

4. The method of claim 1, wherein infusing the lead boot with at least one antibiotic drug further includes mixing the at least one antibiotic into the elastic polymer before molding the lead boot.

* * * * *